(12) United States Patent
Ohtani et al.

(10) Patent No.: US 8,249,319 B2
(45) Date of Patent: Aug. 21, 2012

(54) NUCLEAR MEDICINE DIAGNOSIS APPARATUS AND DIAGNOSTIC SYSTEM USED THERETO

(75) Inventors: Atsushi Ohtani, Kyoto (JP); Tatsuru Imanishi, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 999 days.

(21) Appl. No.: 12/281,125

(22) PCT Filed: Mar. 6, 2007

(86) PCT No.: PCT/JP2007/054283

§ 371 (c)(1),
(2), (4) Date: Aug. 28, 2008

(87) PCT Pub. No.: WO2007/105536

PCT Pub. Date: Sep. 20, 2007

(65) Prior Publication Data

US 2009/0012718 A1    Jan. 8, 2009

(30) Foreign Application Priority Data

Mar. 10, 2006 (JP) ................. 2006-065805

(51) Int. Cl.
*G06K 9/00* (2006.01)
(52) U.S. Cl. ...................... 382/128; 382/131
(58) Field of Classification Search .......... 382/128, 382/131
See application file for complete search history.

(56) References Cited

U.S. PATENT DOCUMENTS 5,841,140 A * 11/1998 Mc Croskey et al. ..... 250/363.03
6,255,655 B1 * 7/2001 Mc Croskey et al. ..... 250/363.03

FOREIGN PATENT DOCUMENTS

JP         07-113873 A    5/1995
JP         08-043536 A    2/1996

OTHER PUBLICATIONS

Supplementary European Search Report for the Application No. EP 07 73 7833 dated Jan. 4, 2010.
Kudomi, Nobuyuki et al., "Rapid Quantitative Measurement of $CMRO_2$ and CBF by Dual Administration of $^{15}O$-labeled Oxygen and Water During a Single PET Scan—A Validation Study and Error Analysis in Anesthetized Monkeys", Journal of Cerebral Blood Flow & Metabolism, 2005, vol. 25, pp. 1209-1224.
Beyer, Thomas et al., "A Combined PET/CT Scanner for Clinical Oncology", The Journal of Nuclear Medicine, 2000, vol. 41, No. 8, pp. 1369-1379.
Shidahara, Miho et al., "Evaluation of a Commercial PET Tomograph-based System for the Quantitative Assessment of rCBF, rOEF and $rOMRO_2$ by Using Sequential Administration of $^{15}O$-labeled Compounds", Annals of Nuclear Medicine, 2002, vol. 16, No. 5, pp. 317-327.
International Search Report for the Application No. PCT/JP2007/054283 mailed Apr. 10, 2007.
* cited by examiner

*Primary Examiner* — Bhavesh Mehta
*Assistant Examiner* — Utpal Shah
(74) *Attorney, Agent, or Firm* — Cheng Law Group, PLLC (57) ABSTRACT

The function of an accumulated amount deriving part 14 can obtain the variation with time of the accumulated amount in the subject based on the radiopharmaceutical in a condition being separated for each radiopharmaceutical, that is, the second variation with time that is a function of the accumulated amount using the first variation with time that is a variation with time of a projection data measured by the projection data deriving part 10. The accumulated image acquisition part 15 acquires the accumulated image of each radiopharmaceutical to be provided for nuclear medicine diagnosis based on the second variations with time separated in this way, enabling the nuclear medicine diagnosis in administration of a variety of radiopharmaceuticals.

27 Claims, 3 Drawing Sheets

NUCLEAR MEDICINE DIAGNOSIS APPARATUS AND DIAGNOSTIC SYSTEM USED THERETO

FIELD OF THE INVENTION

The present invention relates to a nuclear medicine diagnosis apparatus for obtaining data for nuclear medicine of a subject based on radioactive rays generated from the subject with a radiopharmaceutical having administered thereto and to a diagnostic system used therefor. Especially, the present invention relates to a technique of performing image processing with respect to data for nuclear medicine.

RELATED ART

Description will, hereinafter, be given using a PET (Positron Emission Tomography) apparatus as an example for the above-described nuclear medicine diagnosis apparatus, that is, an ECT (Emission Computed Tomography) apparatus. The PET apparatus is configured so as to reconstruct a sectional image of a subject, only when a plurality of γ rays generated by decay of a proton (positron), that is, positron, are detected, and furthermore γ rays are simultaneously detected with a plurality of detectors.

This PET apparatus enables quantitative measurement of various body functions using a measurement with time of a process of chemicals accumulation in a subject structure after administration of a radiopharmaceutical to the subject. For this reason, sectional images obtained by PET apparatus have functional information.

In detail, a description will be given for an example using a human body as a subject. A radiopharmaceutical that is a pair annihilation γ ray radiating matter easily concentrated on a specific part and cell based on a body function of the human body is administered. Then, a functional image of the human body may be picturized (for example, refer to Patent Document 1) by collecting a projection data (referred to also as "emission data") that is an information emitted from a chemical using a PET apparatus.

[Patent Document 1]
JP, 07-113873, A (page 2, FIG. 2)

DESCRIPTION OF THE INVENTION

Problems to be Solved by the Invention

γ rays are monochromatic lights, however, and the PET apparatus detects the γ ray that is a monochromatic light. For this reason, a plurality of examinations that use different radiopharmaceuticals will be necessary in order to obtain different functional images. That is, since repeated operations have to be performed for a pair operations of administration of a certain radiopharmaceutical and examination after specified time elapse from the administration for each radiopharmaceutical that has been administered, the method has given the subject increase of an amount of exposure, and temporal and physical burden.

The present invention has been completed in view of such a situation. The present invention aims at providing a nuclear medicine diagnosis apparatus allowing nuclear medicine diagnosis even in the case of administration of a variety of radiopharmaceuticals, and at providing a diagnostic system used for the diagnosis apparatus.

Means for Solving the Problem

The present invention adopts following constitutions in order to achieve such objects. That is, the present invention provides a nuclear medicine diagnosis apparatus for obtaining data for nuclear medicine of a subject based on radioactive rays generated from the subject having radiopharmaceuticals administered thereto, comprising:

a first measuring device for measuring a first variation with time that is a variation with time of the data for nuclear medicine obtained by a variety of radiopharmaceuticals having been administered;

a deriving device for obtaining the second variation with time, for each radiopharmaceutical, that is a variation with time of an accumulated amount by the radiopharmaceuticals in the subject based on the first variation with time; and an acquiring device for acquiring the accumulated image of each radiopharmaceutical based on the second variation with time.

According to the nuclear medicine diagnosis apparatus of the present invention, the first measuring device for measuring the first variation with time measures the first variation with time that is a variation with time of a data for nuclear medicine obtained by administration of a variety of radiopharmaceuticals, and the deriving device for obtaining the second variation with time obtains, for each of the radiopharmaceutical, the second variation with time that is a variation with time of accumulated amount in the subject by the radiopharmaceutical based on the first variation with time. On one hand, in the case of simultaneous administration of radiopharmaceuticals of mutually different nuclides, since each nuclide has a different half-life with each other, the dose rate of the radioactive rays from the radiopharmaceutical including a nuclide having a shorter half-life decays more quickly than the dose rate of the radioactive rays from the radiopharmaceutical including a nuclide having a longer half-life. On the other hand, even in the case of a radiopharmaceutical including the same nuclide, shift of administration time gives decaying doses different with each other. In this way, the deriving device for obtaining the second variation with time can obtain the second variation with time (the variation with time of an accumulated amount by the radiopharmaceuticals in the subject) in a condition being separated for every radiopharmaceutical, using the first variation with time (the variation with time of the data for nuclear medicine) measured by the first measuring device for measuring the first variation with time. Since the acquiring device for acquiring an accumulated image acquires the accumulated image of each of the radiopharmaceuticals based on these second variations with time separated in this way and provides the images to the nuclear medicine diagnosis, administration of a variety of radiopharmaceuticals will enable the nuclear medicine diagnosis.

In the above-described invention, the second variation with time is a function of an accumulated amount that varies with progress of time, the nuclear medicine diagnosis apparatus preferably comprises a storing device for the function of the accumulated amount that has stored beforehand the function of the accumulated amount of each radiopharmaceutical. Then, the nuclear medicine diagnosis apparatus preferably specifies the radiopharmaceutical in the above-described accumulated image based on the function of the accumulated amount of each radiopharmaceutical that has been stored beforehand by the storing device for the function of the accumulated amount. The nuclear medicine diagnosis apparatus obtains the second variations with time (the variations with time of the accumulated amounts by radiopharmaceuticals in the subject) in the condition of having separated for every radiopharmaceutical, and can acquire the accumulated image of each radiopharmaceutical. Furthermore, the nuclear medicine diagnosis apparatus can also specify the radiopharmaceuticals in the accumulated image by having such a storing device for the function of the accumulated amount that has been stored beforehand the function of the accumulated amount of each radiopharmaceutical.

In an embodiment of the above-described invention, the first measuring device for measuring a first variation with time measures the first variation with time at a plurality of points, when the number of radiopharmaceutical administered is set to M, and the number of unknown number for determining the second variation with time for every radiopharmaceutical is set to N. (M×N) of the unknown number will be given in total, when the number of radiopharmaceutical administered is set to M, the number of the unknown numbers for determining the second variation with time for every radiopharmaceutical is set to N. Here, measurement for a plurality of points, more preferably at least (M×N) points, of the first variation with time by the first measuring device for measuring a first variation with time can give N of the unknown numbers for each radiopharmaceutical, respectively. Determination of the N of the unknown numbers can give the second variation with time and accumulation image for M of radiopharmaceuticals respectively.

In a further detailed example of the above-described embodiment, when the first variation with time is a variation with time of a total dose of the radioactive rays obtained by M of the radiopharmaceuticals being administered;
the Jth radiopharmaceutical is set to $A_J$ (where, J=1, 2, ---, M−1, M), the variation with time of the dose rate by the radiopharmaceutical $A_J$ is set to $F_J(t)$ (where, J=1, 2, ---, M−1, M), the variation with time of an accumulated amount in the radiopharmaceutical $A_J$ that exists in a certain pixel for the second variation with time is set to $a_J(\alpha_J, \beta_J, \gamma_J, ---, t)$ (where, J=1, 2, ---, M−1, and M, and $\alpha_J, \beta_J, \gamma_J, ---$ are the N of unknown numbers), and the variation with time of the total dose is set to E (t),
then the total dose $\int E(t)dt$ of a certain pixel in a certain period width, is represented with the first equation of $$\Sigma_{J=1}^{M}\{\int a_J(\alpha_J,\beta_J,\gamma_J, ---, t)F_J(t)dt\}=\int E(t)dt.$$

The deriving device for obtaining the second variation with time determines the variation with time $a_J(\alpha_J, \beta_J, \gamma_J, ---, t)$ of the accumulated amount in the radiopharmaceutical $A_J$ that exists in a certain pixel for every radiopharmaceutical $A_J$, by determining the N of unknown numbers $\alpha_J, \beta_J, \gamma_J,$ and - - - for obtaining the variation with time $a_J(\alpha_J, \beta_J, \gamma_J, ---, t)$ of the above-described accumulated amount for each radiopharmaceutical $A_J$ based on the first variation with time measured at the a plurality of points and based on the above-described first equation, and by determining the N of the unknown numbers $\alpha_J, \beta_J, \gamma_J, ---$.

In a further detailed example of the above-described embodiment, the variation with time $a_J(\alpha_J, \beta_J, \gamma_J, ---, t)$, that is the second variation with time, of the accumulated amount based on the radiopharmaceutical $A_J$ that exists in a certain pixel (where, J=1, 2, ---, M−1, and M, and $\alpha_J, \beta_J, \gamma_J,$ and - - - are the N unknown numbers) is a function of an accumulated amount that varies with progress of time, and the function of the accumulated amount $a_J(\alpha_J, \beta_J, \gamma_J, ---, t)$ is represented with the second equation of $a_J(\alpha_J, \beta_J, \gamma_J, ---, t)=\alpha_J \cdot \exp(\beta_J \cdot t)+\gamma_J$ represented with the three unknown numbers $\alpha_J, \beta_J,$ and $\gamma_J, \ldots$. The three unknown numbers of $\alpha_J, \beta_J,$ and $\gamma_J$ for obtaining the function of the accumulated amount $a_J(\alpha_J, \beta_J, \gamma_J, ---, t)$ is obtained based on the first variation with time measured at least (M×3) of points and the above-described first equation $(\Sigma_{J=1}^{M}\{\int a_J(\alpha_J, \beta_J, \gamma_J, ---, t)F_J(t)dt\}=\int E(t)dt)$ to determine the three unknown numbers $\alpha_J, \beta_J, \gamma_J$. Thereby, the deriving device for obtaining the second variation with time obtains the function of the accumulated amount $a_J(\alpha_J, \beta_J, \gamma_J, ---, t)$ for each radiopharmaceutical $A_J$.

Incidentally, since the accumulated amount is sharply varied immediately after the administration of the radiopharmaceutical $A_J$, examination (that is, measurement of the first variation with time by the first measuring device for measuring the first variation with time) in such a sharply varying condition is unsuitable. Here, the function of the accumulated amount $a_J(\alpha_J, \beta_J, \gamma_J, ---, t)=\alpha_J \cdot \exp(\beta_J \cdot t)+\gamma_J$ will converge to the $\alpha_J$ after progress of a predetermined period of time (sufficient period of time for examination) after administration of the radiopharmaceutical $A_J$. Here, the only unknown number $\alpha_J$ for each radiopharmaceutical $A_J$ is obtained by setting the function of the accumulated amount $a_J(\alpha_J, \beta_J, \gamma_J, ---, t)$ to $\alpha_J$, and thus the deriving device for obtaining the second variation with time can obtain the function of the accumulated amount $\alpha_J$ for each radiopharmaceutical $A_J$. Accordingly, it is not necessary to obtain other unknown numbers $\beta_J, \gamma_J, ---$, leading to reduction of the number of times of measurement of the first variation with time by the first measuring device for measuring the first variation with time.

In addition, in case of use of a radiopharmaceutical $A_I$ (where, I=1, 2, ---, M−1, M) and $A_J$ (where, J=1, 2, ---, M−1, and M, and I≠J), when the radiopharmaceuticals $A_I$ and $A_J$ are administered at administration point of times shifted with each other, and the shifted administration time is set to based on a point of time of administration of the radiopharmaceutical $A_J$, the variation with time of the dose rate by the radiopharmaceutical $A_I$ may be represented with $F_I(t-t_0)$, and simultaneously the variation with time of a dose rate by the radiopharmaceutical $A_J$ may be represented with $F_J(t)$.

Especially, when two radiopharmaceuticals $A_I$ and $A_J$ are used, and the radiopharmaceuticals $A_I$ and $A_J$ are the same nuclides with each other, a total dose $\int E(t)dt$ of the above-described pixel may be represented with the first equation, $\int a_I(\alpha_I, \beta_I, \gamma_I, ---, t)\{k \cdot F_I(t-t_0)+C_1\}dt+\int a_J(\alpha_J, \beta_J, \gamma_J, ---, t)F_J(t)dt=\int E(t)dt$ (where, k and $C_1$ are constants). The N of unknown numbers $\alpha_J, \beta_J, \gamma_J,$ and - - - for obtaining the variation with time of the accumulated amount for each radiopharmaceutical $A_I$ and $A_J$ of $\alpha_J(\alpha_J, \beta_J, \gamma_J, ---, t)$ may be obtained based on the first variation with time measured at a plurality of points, and on the above-described first equation. And, by thus obtaining the N of unknown numbers $\alpha_J, \beta_J, \gamma_J, ---$, the deriving device for obtaining the second variation with time can obtain the variation with time of the accumulated amount $a_J(\alpha_J, \beta_J, \gamma_J, ---, t)$ for each of the radiopharmaceuticals $A_I$ and $A_J$ that exists in a certain pixel for each of the radiopharmaceuticals $A_I$ and $A_J$.

Furthermore, when two radiopharmaceuticals $A_I$ and $A_J$ are used, and the radiopharmaceuticals $A_I$ and $A_J$ are different nuclides with each other, a total dose $\int E(t)dt$ of the above-described pixel may be represented with the first equation $\int a_I(\alpha_I, \beta_I, \gamma_I, ---, t)\{F_I(t-t_0)+C_2\}dt+\int a_J(\alpha_J, \beta_J, \gamma_J, ---, t)F_J(t)dt=\int E(t)dt$ (where, $C_2$ is a constant). The N of unknown numbers $\alpha_J, \beta_J, \gamma_J,$ and - - - for obtaining the variation with time of the accumulated amount for every radiopharmaceutical $A_I$ and $A_J$ of $a_J(\alpha_J, \beta_J, \gamma_J, ---, t)$ may be obtained based on the first variation with time measured at a plurality of points, and on the above-described first equation. And, by thus obtaining the N of unknown numbers $\alpha_J, \beta_J, \gamma_J,$ and - - -, the deriving device for obtaining the second variation with time can obtain the variation with time of the accumulated amount $a_J(\alpha_J, \beta_J, \gamma_J, ---, t)$ for each of the radiopharmaceuticals $A_I$ and $A_J$ that exists in a certain pixel for every radiopharmaceuticals $A_I$ and $A_J$.

As described above, a variety of radiopharmaceuticals to be administered may be the same nuclide with each other, and may be different nuclide with each other. Accordingly, the data for nuclear medicine obtained by administration of a variety of radiopharmaceuticals may also include the data obtained by administration of the radiopharmaceuticals of the same nuclide at points of time shifted with each other, and may also include the data obtained by administration of the radiopharmaceuticals of different nuclide with each other.

In the above-described invention, the nuclear medicine diagnosis apparatus of the present invention may comprise an input device for inputting a plurality of information about the data for nuclear medicine. Information about a variety of radiopharmaceuticals to be administer by examination at the same time, for example, kinds of the radiopharmaceuticals, half-life, administration point of time (or measuring point of time), etc. may be inputted as the information about the data for nuclear medicine.

Incidentally, in the above-described invention, the nuclear medicine diagnosis apparatus of the present invention may comprise an output device for separately output-displaying the accumulated image of each radiopharmaceutical acquired by the acquiring device for acquiring the accumulated image, or may comprise an output device for changing the color and for superimposed output-displaying. Thereby, separate output display of the accumulated image of each radiopharmaceutical acquired by the acquiring device for acquiring the accumulated image, or superimposed output display using different colors can provide identification of the accumulated image for every radiopharmaceutical, leading to provision of useful information to nuclear medicine diagnosis.

Incidentally, an embodiment of the present invention may be applied to a diagnostic system used for the nuclear medicine diagnosis apparatus according to the above-described invention. That is, the diagnostic system comprises the nuclear medicine diagnosis apparatus and an X-ray CT apparatus. The nuclear medicine diagnosis apparatus obtains data for nuclear medicine of the subject based on radioactive rays generated from the subject having the radiopharmaceutical administered thereto. The X-ray CT apparatus obtains data for the X-ray CT based on the X-rays having been emitted from the outside of the subject and having transmitted through the subject. The nuclear medicine diagnosis apparatus comprises a first measuring device for measuring a first variation with time that is a variation with time of data for nuclear medicine obtained by a variety of radiopharmaceuticals having been administered; a deriving device for obtaining a second variation with time, for each radiopharmaceutical, that is a variation with time of an accumulated amount by the radiopharmaceuticals in the subject based on the first variation with time; and an acquiring device for acquiring an accumulated image of each radiopharmaceutical based on the second variation with time.

In the case of the diagnostic system of the present invention, the X-ray CT apparatus obtains the data for the X-ray CT based on the X-rays having been emitted from the outside of the subject and having transmitted through the subject, and the nuclear medicine diagnosis apparatus acquires an accumulated image of each radiopharmaceutical, respectively. Incidentally, the tomogram image in the data for X-ray CT and each accumulated image may be superimposed for superimposed outputting. Absorption correction of the data for nuclear medicine may be performed based on use of the data for the X-ray CT as an absorption correction data, and measurement of the first variation with time and derivation of the second variation with time or acquisition of the accumulated image of each radiopharmaceutical may be performed based on the data for nuclear medicine after the absorption correction.

Also in the diagnostic system of the present invention, as in the same manner of the nuclear medicine diagnosis apparatus of the present invention, the data for nuclear medicine obtained by administration of a variety of radiopharmaceuticals may include the data obtained by administration of radiopharmaceuticals of the same nuclide at points of time shifted with each other, and may also include the data obtained by administration of the radiopharmaceuticals of different nuclide with each other.

Similarly in the nuclear medicine diagnosis apparatus of the present invention, the diagnostic system of the present invention may comprise an input device for inputting a plurality of information about data for nuclear medicine.

Incidentally, similarly in the nuclear medicine diagnosis apparatus of the present invention, the diagnostic system of the present invention may comprise an output device for separately output-displaying the accumulated image of each radiopharmaceutical acquired by the acquiring device for acquiring the accumulated image, or an output device for changing the color and for superimposed outputting.

Effect of the Invention

According to the nuclear medicine diagnosis apparatus according to the present invention and the diagnostic system used therefor, the deriving device for obtaining the second variation with time can obtain the second variation with time (variation with time of the accumulated amount by radiopharmaceutical in the subject) in a condition separated for each radiopharmaceutical using the first variation with time (the variation with time of data for nuclear medicine) measured by the first measuring device for measuring the first variation with time. The acquiring device for acquiring the accumulated image acquires the accumulated image of each radiopharmaceutical to provide the accumulated image for nuclear medicine diagnosis based on the second variations with time thus separated, thereby providing the nuclear medicine diagnosis based on administration of a variety of radiopharmaceuticals.

BRIEF DESCRIPTION OF THE DRAWINGS

In FIG. 1, (a) illustrates a side view and a block diagram of a PET (Positron Emission Tomography) apparatus by Example 1, and (b) illustrates an enlarged view giving a detailed constitution of a γ ray detector;

DESCRIPTION OF NOTATIONS

8: Input part
9: Output part
10: Projection data deriving part
14: Function of an accumulated amount deriving part
15: Accumulated image acquisition part
16*a*: Function of an accumulated amount storing part
M: Subject Example 1

Figure 1:
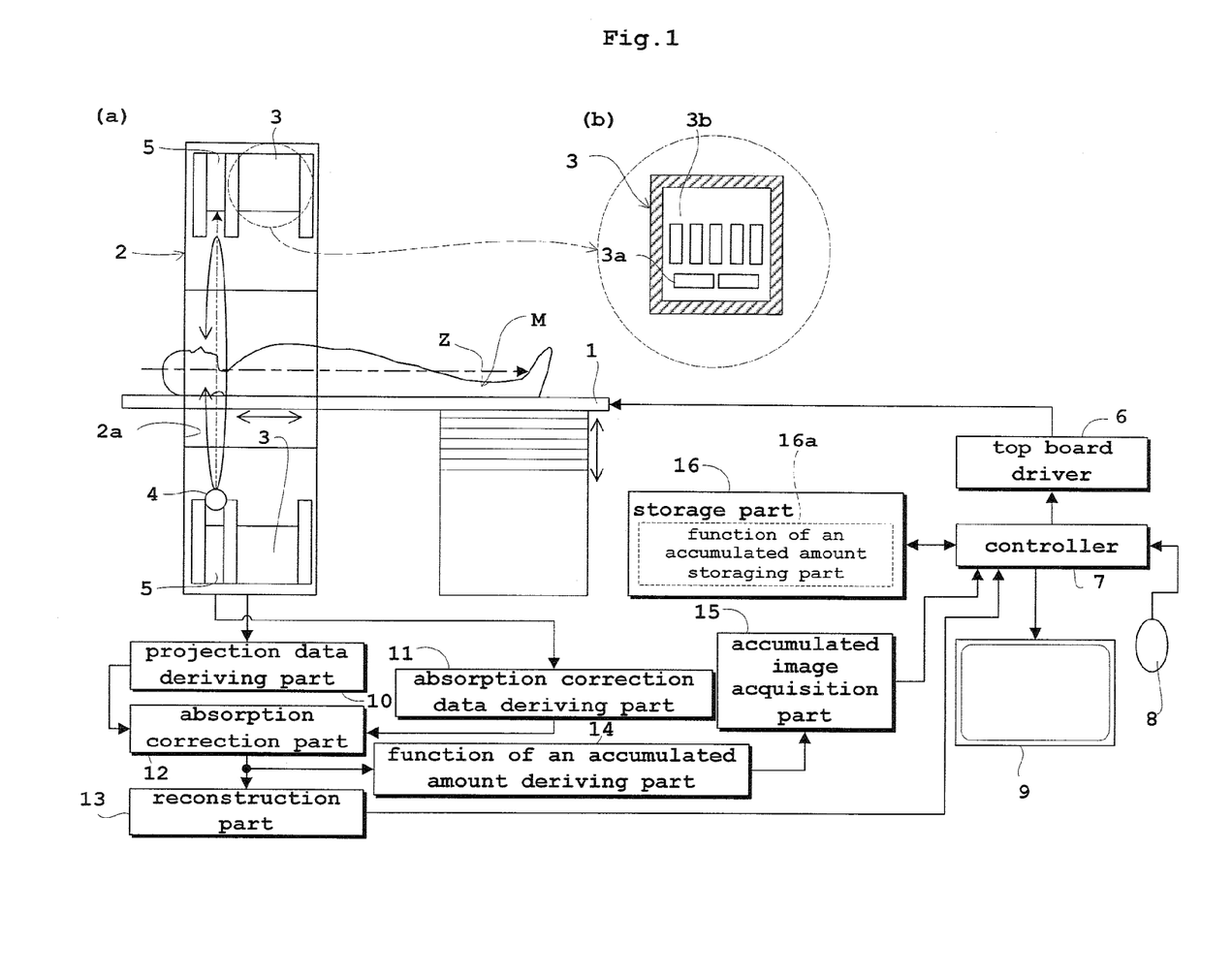

Hereinafter, Example 1 of the present invention will be described with reference to drawings. This FIG. 1 is a side view and a block diagram of a PET (Positron Emission Tomography) apparatus related to Example 1. The description will be given using the PET apparatus as a nuclear medicine diagnosis apparatus in Example 1, and also in Example 2 to be mentioned later.

The PET apparatus according to the Example 1 is provided with a top board 1 for supporting a subject M as illustrated in FIG. 1. This top board 1 can ascend and descend up and down, and can move in parallel along with the body axis Z of the subject M. Such a system allows scanning of the subject M mounted on the top board 1 sequentially from the head, to the abdomen and the foot through the opening 2a of the gantry 2 to be mentioned later, providing diagnostic data, such as projection data and a tomogram image of the subject M. These diagnostic data are equivalent to the data for nuclear medicine in the present invention.

The PET apparatus according to the Example 1 comprises, in addition to the top board 1, the gantry 2 having the opening 2a, and a plurality of scintillator blocks 3a closely disposed with each other and a plurality of photomultipliers 3b. The scintillator block 3a and the photomultiplier 3b are disposed to form a ring shape so as to surround the circumference of the body axis Z of the subject M, and they are embedded in the gantry 2, as illustrated in FIG. 1 (b). The photomultiplier 3b is disposed outside the scintillator block 3a. Example of the detailed disposition of the scintillator block 3a includes a case wherein two scintillator blocks 3a are disposed in a line in a direction parallel to the body axis Z of the subject M, and a large number of scintillator blocks 3a are disposed in a line around the body axis Z of the subject M. The scintillator block 3a and the photomultiplier 3b form the γ ray detector 3 for projection data (referred to as "emission data") to be mentioned later.

Incidentally, the Example 1 has a point radiation source 4 and a γ ray detector 5 for absorption correction data (referred to as "transmission data") to be mentioned later. The γ ray detector 5 for absorption correction data has a scintillator block and a photomultiplier like the γ ray detector 3 for the projection data. The point radiation source 4 is a radiopharmaceutical to be administered in the subject M, that is, a source for emitting radioactive rays of the same kind (in the Example 1 γ ray) as by the radioisotope (RI), and is disposed in the exterior of the subject M. In the Example 1, it is embedded in the gantry 2. The point radiation source 4 rotates around the body axis Z of the subject M.

In addition, the PET apparatus according to the Example 1 has a top board driver 6, a controller 7, an input part 8, an output part 9, a projection data deriving part 10, an absorption correction data deriving part 11, an absorption correction part 12, a reconstruction part 13, a function of the accumulated amount deriving part 14, and an accumulated image acquisition part 15. The top board driver 6 is a mechanism for driving the top board 1 in the above-described manner, and comprises a motor etc. (not shown).

The controller 7 generally controls each part constituting the PET apparatus by the Example 1. The controller 7 comprises a central processing unit (CPU) etc.

The input part 8 sends out the data and the command inputted by the operator to the controller 7. The input part 8 comprises pointing devices represented by a mouse, a keyboard, a joystick, a trackball, a touch panel, etc. The output part 9 comprises indicators represented by a monitor etc., a printer, etc.

In the Example 1, and also in Example 2 to be described later, the input part 8 is constituted so as to input a plurality of information about the data for nuclear medicine. The information about a variety of radiopharmaceuticals to be administered in one examination, for example, kinds (FDG, FES, etc.) of the radiopharmaceuticals, a half-life, an administration point of time (or measuring point of time) etc. can be inputted as information about the data for nuclear medicine. The input part 8 is equivalent to the input device in the present invention.

In the Example 1, and also in the Example 2 to be described later, the display of the output part 9 displays the accumulated image of each radiopharmaceutical acquired by the accumulated image acquisition part 15 separately, or changes the color for superimposed output-displaying. The separate output displaying of the accumulated image of each radiopharmaceutical acquired by the accumulated image acquisition part 15 or the superimposed output display with a changed color allows identification of the accumulated image for each radiopharmaceutical, providing useful information for nuclear medicine diagnosis. The output part 9 is equivalent to the output device in the present invention.

The storing part 16 comprises storage media represented by ROM (Read-only Memory), RAM (Random-Access Memory), etc. In the Example 1, diagnostic data processed by the projection data deriving part 10 or the reconstruction part 13, an absorption correction data obtained by the absorption correction data deriving part 11, a function of the accumulated amount for each radiopharmaceutical obtained by the function of the accumulated amount deriving part 14, and an accumulated image of each radiopharmaceutical acquired by the accumulated image acquisition part 15 are written in the RAM to be stored, and are read out from the RAM if needed. The ROM stores beforehand a program for performing various kinds of nuclear medicine diagnoses, etc. Nuclear medicine diagnosis corresponding to the program is performed by execution of the controller 7 of the program, respectively. In the Example 1, the storing part 16 comprises a function of the accumulated amount storing part 16a having stored beforehand the function of the accumulated amount of each radiopharmaceutical.

The projection data deriving part 10, the absorption correction data deriving part 11, the absorption correction part 12, the reconstruction part 13, the function of the accumulated amount deriving part 14, and the accumulated image acquisition part 15 demonstrate the function thereof by, for example, executing the commands inputted by the controller 7 of the programs stored by the ROM of storage medium represented by the above-described storing part 16 etc., or by the pointing devices represented by the input part 8 etc.

The scintillator block 3a converts into a light a γ ray generated from the subject M having a radiopharmaceutical administered, and the photomultiplier 3b photo-electric converts the converted light, and outputs as an electric signal. It sends the electric signal as an image information (pixel) into the projection data deriving part 10.

In detail, when a radiopharmaceutical is administered in the subject M, the positron of the positron emission type RI annihilates to generate two γ rays. The projection data deriving part 10 checks the position of the scintillator block 3a, and the incidence timing of the γ rays, and judges as an appropriate data using a sent-in image information only when the γ rays enter simultaneously in the two scintillator blocks 3a disposed in opposed positions with each other on both sides of the subject M. When a γ ray enters only into one scintillator block 3a, the projection data deriving part 10 recognizes the incidence as a noise, not as a γ ray generated by annihilation of positron, and judges the image information then sent in as a noise to be rejected.

A variety of radiopharmaceuticals is administered to the subject in the Example 1. Accordingly, the image information by a variety of radiopharmaceuticals are obtained as one image information in a group by judgment by the projection data deriving part 10. That is, the data judged as appropriate by this projection data deriving part 10 includes the image information for each radiopharmaceutical in a mixed state without being classified. In the Example 1, this image information may be recognized as a total dose (the total counting value) of the γ ray, and the projection data deriving part 10 measures the γ ray a plurality of times (for example, 6 times) for every predetermined period of time (in case of 18 minutes of inspection period, every 3 minutes) to obtain the variation with time of the total dose. Accordingly, in the case of 6 measurements of the γ ray in every 3 minutes in case of the inspection period of time for 18 minutes, the variations with time of the image information (total dose, that is, the total counting value, of the γ ray) after 3 minutes; 6 minutes (=3 minutes×2 times); 9 minutes (=3 minutes×3 times); 12 minutes (=3 minutes×4 times); 15 minutes (=3 minutes×5 times); and 18 minutes (=3 minutes×6 times) will be measured, respectively. The variation with time of the image information (total dose of the γ ray) is equivalent to the first variation with time (the variation with time of the data for nuclear medicine) in the present invention, and the projection data deriving part 10 is equivalent to the first measuring device for measuring the first variation with time in the present invention.

The image information (total dose of the γ ray) sent into the projection data deriving part 10 is then sent into the absorption correction part 12 as a projection data. The absorption correction data (transmission data) sent into the absorption correction part 12 from the absorption correction data deriving part 11 are applied to the projection data sent into the absorption correction part 12, and thus the projection data is corrected into a projection data in consideration of the absorption of the γ ray in the body of the subject M. Actually, this corrected variation with time of the projection data (total dose, that is, the total counting value, of the γ ray) is used as the first variation with time (the variation with time of the data for nuclear medicine).

The point radiation source 4, while rotating around the body axis Z of the subject M, emits γ rays to the subject M, and the scintillator blocks (not shown) of the γ ray detector 5 for the absorption correction data convert the emitted γ rays into a light. Subsequently, the photomultiplier (not shown) of the γ ray detector 5 performs photo-electric conversion of the converted light, and outputs as an electric signal, and sends the electric signal into the absorption correction data deriving part 11 as an image information (pixel).

The absorption correction data are obtained based on the image information sent into the absorption correction data deriving part 11. The absorption correction data deriving part 11 uses an operation representing the relationship between the absorption coefficient of the γ ray or the X-rays, and the energy, and converts the projection data for CT, that is, the distribution data of the X ray absorption coefficient, into a distribution data of the γ ray absorption coefficient, obtaining the distribution data of the γ ray absorption coefficient as the absorption correction data. The derived absorption correction data are then sent to the above-described absorption correction part 12.

The corrected projection data is sent into the reconstruction part 13. The reconstruction part 13 reconstructs the projection data, and it obtains a tomogram image influenced with the absorption of the γ ray in the body of the subject M. In this manner, the absorption correction part 12 and the reconstruction part 13 correct the projection data based on the absorption correction data, and correct the tomogram image. The corrected tomogram image is sent into the output part 9 through the controller 7.

The tomogram images are in a mixed state without being classified for each radiopharmaceutical. In order to separate the data for each radiopharmaceutical, the present invention has the above-described function of the accumulated amount deriving part 14 or the accumulated image acquisition part 15. Next, the function of the accumulated amount deriving part 14 and the accumulated image acquisition part 15 are then described.

The function of the accumulated amount deriving part 14 obtains the variation with time of the accumulated amount by the radiopharmaceutical in the subject M for each radiopharmaceutical. The accumulated amount is represented as a function of the accumulated amount that varies with progress of time. The function of the accumulated amount is equivalent to the second variation with time (variation with time of the accumulated amount in subject by radiopharmaceutical) in the present invention, and the function of the accumulated amount deriving part 14 is equivalent to the deriving device for obtaining the second variation with time in the present invention.

The accumulated image acquisition part 15 acquires the accumulated image of each radiopharmaceutical based on the function of the accumulated amount mentioned above. The accumulated image acquisition part 15 is equivalent to the acquiring device for acquiring the accumulated image in the present invention.

Figure 2:
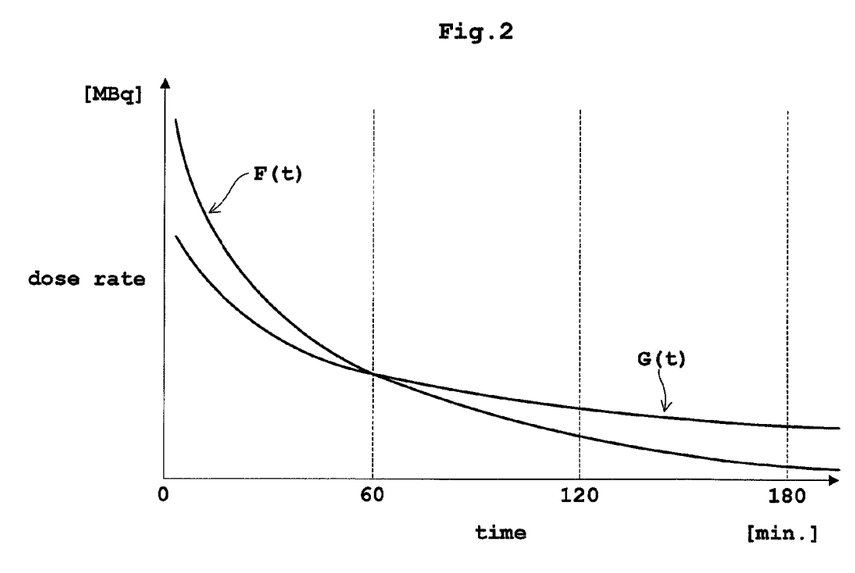
FIG. 2 illustrates a graph for a schematic variation with time of a dose rate.
Figure 3:
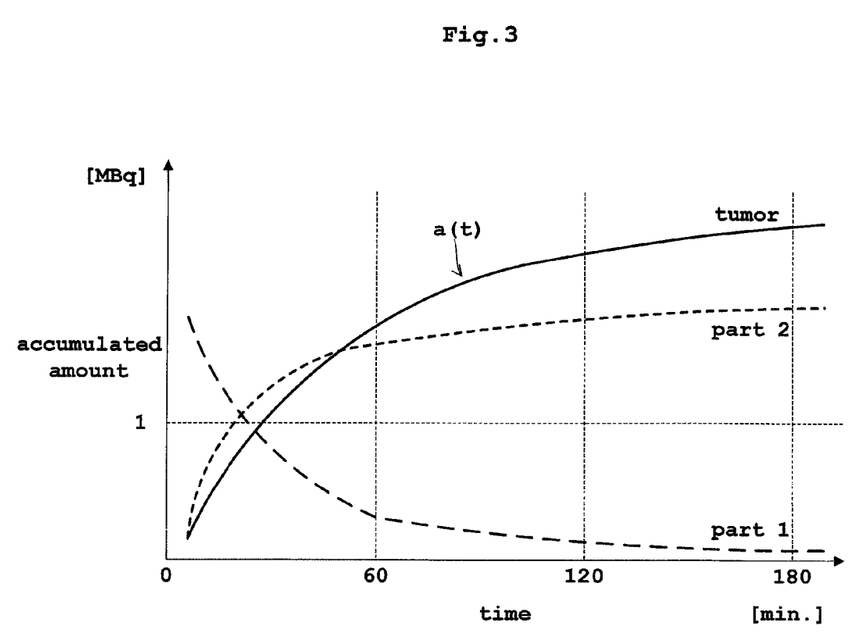
FIG. 3 illustrates a schematic graph for a function of the accumulated amount.

Next, the above-described total dose of the γ ray and the function of the accumulated amount, and the variation with time of the dose rate will be described with reference to FIG. 2 and FIG. 3. FIG. 2 is a graph schematically illustrating a variation with time of a dose rate, and FIG. 3 is a graph schematically illustrating a function of the accumulated amount.

The number of radiopharmaceuticals to be administered is set to M, and the Jth radiopharmaceutical is set to $A_J$ (where, J=1, 2, - - - , M−1, M). When the variation with time of dose rate by the radiopharmaceutical $A_J$ is set to $F_J(t)$ (where, J=1, 2, - - - , M−1, M), $F_J(t)$ is represented with following equation (1).

$$F_J(t)=N_J \cdot \exp(-\lambda_J t) \qquad (1)$$

where, $N_J$ is a number of radionuclide of the radiopharmaceutical $A_J$ upon administration, and $\lambda_J$ is a decay constant of the radiopharmaceutical.

When a variation with time (that is, a function of an accumulated amount) of an accumulated amount in the radiopharmaceutical $A_J$ that exists in a certain pixel is set to $a_J(\alpha_J, \beta_J, \gamma_J, ---, t)$ (where, J=1, 2, - - - , M−1, and M, $\alpha_J, \beta_J, \gamma_J$, and - - - are N number of unknown numbers), and a variation with time of a total dose is set to E(t), the total dose $\int E(t)dt$ of a certain pixel in a certain period width, is represented with a following equation (2).

$$\Sigma_{J=1}^{M}\{\int a_J(\alpha_J,\beta_J,\gamma_J,---,t)F_J(t)dt\}=\int E(t)dt \qquad (2)$$

The above-described equation (2) is equivalent to the first equation in the present invention.

When the number of unknown numbers $\alpha_J, \beta_J, \gamma_J$, and - - - for determining the function of the accumulated amount $a_J(\alpha_J, \beta_J, \gamma_J, ---, t)$ for each radiopharmaceutical $A_J$ is N, the sum total of the unknown number is (M×N). Here, the variation with time of a plurality of points, more preferably at least (M×N) of points, of the projection data obtained by absorption correction that is equivalent to the first variation with time is measured, and thereby N of unknown numbers may be obtained for every radiopharmaceutical $A_J$, respectively. By obtaining this N of unknown numbers, the function of the accumulated amount $a_1(\alpha_J, \beta_J, \gamma_J, ---, t)$, $a_2(\alpha_J, \beta_J, \gamma_J, ---, t)$, $---$, $a_j(\alpha_J, \beta_J, \gamma_J, ---, t)$, $---$, $a_{M-1}(\alpha_J, \beta_J, \gamma_J, ---, t)$, $a_M(\alpha_J, \beta_J, \gamma_J, ---, t)$ that are equivalent to the second variations with time for each M of radiopharmaceutical, and the accumulated image may be obtained.

Here, a case where the number of unknown number for determining the function of the accumulated amount $a_j(\alpha_J, \beta_J, \gamma_J, ---, t)$ for each radiopharmaceutical $A_J$ is 3 will be described. In this case, N=3. Here, the function of the accumulated amount $a_j(\alpha_J, \beta_J, \gamma_J, ---, t)$ is assumed to take a specific function as following equation (3).

$$a_j(\alpha_J, \beta_J, \gamma_J, ---, t) = \alpha_J \cdot \exp(\beta_J \cdot t) + \gamma_J \quad (3)$$

where, $\alpha_J$, $\beta_J$, and $\gamma_J$ are the above-described 3 unknown numbers for each radiopharmaceutical $A_J$, and they are (M×3) of unknown numbers in total. The above-described equation (3) is equivalent to the second equation in the present invention.

Here, a case where the number of radiopharmaceuticals administered is 2 will be described. In this case, M=2. When the radiopharmaceutical $A_1$ is set to A, the radiopharmaceutical $A_2$ is set to B, $F_1(t)$ is set to F(t), $F_2(t)$ is set to G(t), $N_1$ is set to $N_a$, and $N_2$ is set to $N_b$, then F(t) and G(t) are represented with the following equations (4) and (5) from the above-described equation (1).

$$F(t) = N_a \cdot \exp(-\lambda_1 \cdot t) \quad (4)$$

$$G(t) = N_b \cdot \exp(-\lambda_2 \cdot t) \quad (5)$$

The variation with time F(t) of the dose rate by the radiopharmaceutical A and the variation with time G(t) of the dose rate by the radiopharmaceutical B will be, for example, represented with a graph of FIG. 2.

When $a_1(\alpha_J, \beta_J, \gamma_J, ---, t)$ is set to a(t) and $a_2(\alpha_J, \beta_J, \gamma_J, ---, t)$ is set to b(t), then a(t) is the function of the accumulated amount by the radiopharmaceutical A that exists in a certain pixel, and b(t) is the function of the accumulated amount by the radiopharmaceutical B that exists in a certain pixel. In a certain period width, the total dose $\int E(t)dt$ of a certain pixel is represented with a following equation (6) from the above-described equation (2).

$$\int a(t)F(t)dt + \int b(t)G(t)dt = \int E(t)dt \quad (6)$$

The function of the accumulated amount a(t) and b(t), are represented with the following equations (7) and (8) from the above-described equation (3).

$$a(t) = \alpha_1 \cdot \exp(\beta_1 \cdot t) + \gamma_1 \quad (7)$$

$$b(t) = \alpha_2 \cdot \exp(\beta_2 \cdot t) + \gamma_2 \quad (8)$$

The function of the accumulated amount a(t) by the radiopharmaceutical A that exists in a certain pixel is, for example, represented with a graph of FIG. 3.

The function of the accumulated amount storing part 16a beforehand stores the graph as in the FIG. 3 as the function of the accumulated amount $a_j(\alpha_J, \beta_J, \gamma_J, ---, t)$ of each radiopharmaceutical. In order to prepare such a graph beforehand, one radiopharmaceutical is administered as in the conventional manner, and operations for measuring the variation with time of the accumulated amount in the subject M by the radiopharmaceutical are repeatedly done for every radiopharmaceutical. FIG. 3 illustrates the functions of the accumulated amount for every part where radiopharmaceutical has accumulated, respectively. The solid line illustrates a tumor and the dotted line illustrate the parts 1 and 2 other than the tumor, respectively. An example of the part 2 where the function is saturated while increasing is the brain etc., and an example of the part 1 where the function is saturated while decreasing is the liver. The function of the accumulated amount prepared beforehand is compared with the function of the accumulated amount prepared this time, respectively, and thereby it is possible to specify the radiopharmaceutical by the nearest function of the accumulated amount as a radiopharmaceutical in the accumulated image. Thus, the radiopharmaceutical in the above-described accumulated image is preferably specified based on the function of the accumulated amount $a_j(\alpha_J, \beta_J, \gamma_J, ---, t)$ of each radiopharmaceutical beforehand stored in the function of the accumulated amount storing part 16a. The function of the accumulated amount storing part 16a is equivalent to the storing device for the function of an accumulated amount in the present invention.

Incidentally, when the number of radiopharmaceuticals to be administered is 2, and the number of unknown number is 3, (2×3)=6 of unknown numbers in total $\alpha_1, \beta_1, \gamma_1, \alpha_2, \beta_2,$ and $\gamma_2$ are given for the radiopharmaceuticals A and B from the above-described equations (7) and (8). Therefore, as described above the measurement of γ ray in every 3 minutes should just be performed for inspection period of time of 6 times in 18 minutes. The variation with time of the projection data is measured by at least 6 times, and thus three unknown numbers (6 in total) may be obtained respectively for each radiopharmaceutical A and B. The function of the accumulated amount a (t) and b (t) of the two radiopharmaceuticals A and B, and accumulated images may be obtained by obtaining the three unknown numbers.

Incidentally, the total accumulated amount can be obtained by integrating the obtained function of the accumulated amount $a_j(\alpha_J, \beta_J, \gamma_J, ---, t)$ for all the inspection period of time, and then the accumulated image for every radiopharmaceutical may be acquired.

Here, since the accumulated amount widely varies as illustrated in FIG. 3 immediately after administration of the radiopharmaceutical $A_J$, thus, examination (that is, measurement of the variation with time of the image information [the total dose of γ ray] equivalent to the first variation with time by the projection data deriving part 10 equivalent to the first measuring device for measuring the first variation with time) in the condition of varying widely is unsuitable. For this reason, when a predetermined period of time (sufficient period of time, in use of FDG as a radiopharmaceutical, approximately 60 minutes) has passed after administration of the radiopharmaceutical $A_J$, the function of the accumulated amount $a_j(\alpha_J, \beta_J, \gamma_J, ---, t) = \alpha_J \cdot \exp(\beta_J \cdot t) + \gamma_J$ represented with the above-described equation (3) will converge to $\alpha_J$. Here, the function of the accumulated amount $a_j(\alpha_J, \beta_J, \gamma_J, ---, t)$ is set as $\alpha_J$, and only the unknown number $\alpha_J$ for each radiopharmaceutical $A_J$ is obtained, and thus the function of the accumulated amount deriving part 14 can obtain the function of the accumulated amount $\alpha_J$ for every radiopharmaceutical $A_J$. Accordingly, it is not necessary to obtain other unknown numbers $\beta_J, \gamma_J, ---$, and therefore the number of times of measurement of the variation with time of image information (total dose of the γ ray) by the projection data deriving part 10 can be reduced.

For example, when the number of radiopharmaceuticals to be administered is 2, $a_1(\alpha_J, \beta_J, \gamma_J, ---, t)$ is set to a(t), and $a_2(\alpha_J, \beta_J, \gamma_J, ---, t)$ is set to b(t), as described above. Then, $a(t) = \alpha_1$, and simultaneously $b(t) = \alpha_2$ from the above-described equations (7) and (8), and by setting $a_j(\alpha_J, \beta_J, \gamma_J, ---, t)$ to $\alpha_J$. Accordingly, since the unknown number is 2 in total, the variation with time of the projection data may just be measured by 2 times.

So far, administration point of time at the same timing of the radiopharmaceuticals has been described, and it is also possible to shift the administration point or time. In detail, when a certain radiopharmaceutical $A_I$ (where, I=1, 2, - - -, M−1, M) and $A_J$ (where, J=1, 2, - - -, M−1 and M, I≠J) are used, the administration point of time of the radiopharmaceutical $A_I$ and $A_J$ are shifted with each other, and the shifted administration point of time is set $t_0$. When based on the point of time at which the radiopharmaceutical $A_J$ is administered, the variation with time of the dose rate by the radiopharmaceutical $A_I$ may be represented with $F_I(t-t_0)$, and the variation with time of the dose rate by the radiopharmaceutical $A_J$ may be represented with $F_J(t)$. When the number of radiopharmaceuticals to be administered is 2, I=1 and J=2, and the radiopharmaceutical $A_I$ may be regarded as $A_1$, and the radiopharmaceutical $A_J$ as $A_2$. As described above, the radiopharmaceutical $A_1$ is A and the radiopharmaceutical $A_2$ is B.

Especially, in the case where the radiopharmaceutical $A_I$(that is, A) and $A_J$(that is, B) are the same nuclide with each other, as described above, I=1 and J=2, $F_I(t)$ and (=$F_1(t)$) is F(t), and $F_J(t)$ and (=$F_2(t)$) is G(t), furthermore $a_1(\alpha_J, \beta_J, \gamma_J, ---, t)$ is a(t), and $a_2(\alpha_J, \beta_J, \gamma_J, ---, t)$ is b(t). Then, the total dose $\int E(t)dt$ of the above-described pixel may be deformed as the above-described equation (2) from the following equation (9).

$$\int a(t)\{k \cdot F(t-t_0)+C_1\}dt + \int b(t)G(t)dt = \int E(t)dt \qquad (9)$$

The above-described equation (9) is equivalent to the first equation in the present invention. Here, k and $C_1$ are constants.

Incidentally, when the radiopharmaceutical $A_I$(that is, A) and $A_J$(that is, B) are different nuclides with each other, in the same way, the total dose $\int E(t)dt$ of the pixel may be deformed as the above-described equation (2) from following equation (10).

$$\int a(t)\{F(t-t_0)+C_2\}dt + \int b(t)G(t)dt = \int E(t)dt \qquad (10)$$

The above-described equation (10) is equivalent to the first equation in the present invention. Here, $C_2$ is a constant.

When the point of time of administering the radiopharmaceutical $A_J$(that is, B) is set as basis, the variation with time of the dose rate by the radiopharmaceutical $A_I$(that is, A) is represented with $F_I(t-t_0)$ as described above, then the variation with time of the dose rate by the radiopharmaceutical $A_J$ is represented with $F_J(t)$, and they may be further represented with the following equations (11) and (12) from the above-described equations (4) and (5).

$$F(t-t_0)=N_a \cdot \exp\{-\lambda_1 \cdot (t-t_0)\} \qquad (11)$$

$$G(t)=N_b \cdot \exp(-\lambda_2 \cdot t) \qquad (12)$$

Here, when the radiopharmaceuticals A and B are the same nuclides with each other, they have the equal decay constant, and then $\lambda_2$ in the above-described (12) equation will be $\lambda_1$.

In case being represented with the above-described equation (11), k=$N_a/N_b$ for k in the above-described equation (9) that is the first equation in case of the radiopharmaceuticals A and B being the same nuclides with each other, and $C_1=N_a \cdot \exp(-\lambda \cdot t_0)$ for $C_1$. In case of being represented with the above-described equation (12), on the other hand, $C_2=N_a \cdot \exp(\lambda_1 \cdot t_0)$ for $C_1$ in the above-described (10) equation that is the first equation in case of the radiopharmaceuticals A and B varying with each other in nuclide.

According to the PET apparatus by the Example 1 comprising the above-described constitution, the projection data deriving part 10 measures the first variation with time that is the variation with time of the data for nuclear medicine (here, total dose of the γ ray) obtained by administration of a variety of radiopharmaceuticals. Then, the function of the accumulated amount deriving part 14 obtains the second variation with time that is the variation with time (here, the function of the accumulated amount) of the accumulated amount in the subject of the radiopharmaceuticals for each radiopharmaceutical based on the first variation with time. In the case of simultaneous administration of radiopharmaceuticals of different nuclide with each other, each radiopharmaceutical has a different half-life based on the nuclide, and therefore the dose rate of the radioactive rays from the radiopharmaceutical including the nuclide having a shorter half-life decays more quickly than the dose rate of the radioactive rays from the radiopharmaceutical including the nuclide having a longer half-life. Even when the radiopharmaceuticals of the same nuclide are used on the other hand, they give different dose of decay in administration in the shifted administration point of time. In this way, the function of the accumulated amount deriving part 14 can obtain the second variation with time (the variation with time of the accumulated amount in the subject by the radiopharmaceutical) in a condition separated for each radiopharmaceutical, using the first variation with time (the variation with time of the data for nuclear medicine) measured by the projection data deriving part 10. Since the accumulated image acquisition part 15 acquires the accumulated images of each radiopharmaceutical and utilizes them for nuclear medicine diagnosis based on these second variations with time separated in this way, nuclear medicine diagnosis in administration of a variety of radiopharmaceuticals may be attained.

Incidentally, the nuclear medicine diagnosis has been performed in the past based on the premise that the number of radiopharmaceutical to be administered is one, and the radiopharmaceutical and the accumulation spot are known beforehand. In administration of a variety of radiopharmaceuticals, as in the Example 1, however, brought will be an effect for the radiopharmaceutical and the accumulation spots to be obtained by separation for each radiopharmaceutical, even when each radiopharmaceutical and the accumulation spots are not known beforehand. Accordingly, the present invention is useful, for example, as in the diagnoses in complete medical checkup, where each radiopharmaceutical and accumulation spot are not obtained beforehand.

In the Example 1, the second variation with time is a function of the accumulated amount that varies with progress of time. The PET apparatus has the function of the accumulated amount storing part 16a that stores beforehand the function of the accumulated amount of each radiopharmaceutical, and it specifies the radiopharmaceutical in the accumulated image based on the function of the accumulated amount of each radiopharmaceutical beforehand stored by the function of the accumulated amount storing part 16a. It obtains the second variation with time (the variation with time of the accumulated amount in the subject by the radiopharmaceutical) in a condition separated for each radiopharmaceutical, then it can acquire the accumulated image of each radiopharmaceutical, and furthermore it can also specify the radiopharmaceutical in the accumulated image by the function of the accumulated amount storing part 16a that stores beforehand the function of the accumulated amount of such each radiopharmaceutical.

In the Example 1, the first variation with time is a variation with time of a total dose of radioactive rays (here, γ rays) obtained by administering M of radiopharmaceuticals, the Jth radiopharmaceutical is set as $A_J$ (here, J=1, 2, - - -, M−1, M), and the variation with time of the dose rate by the radiopharmaceutical $A_J$ is set as $F_J(t)$ (here, J=1, 2, - - - , M−1, M). Furthermore, in the second variation with time, a variation with time of the accumulated amount in the radiopharmaceutical $A_J$ in a certain pixel is set as $a_J(\alpha_J, \beta_J, \gamma_J, - - - , t)$ (here, J=1, 2, - - - , M−1 and M, $\alpha_J, \beta_J, \gamma_J,$ and - - - N unknown numbers), and a variation with time of the total dose is set to E(t). Here, the total dose $\int E(t)\,dt$ in a certain pixel in a certain period width is represented with the above-described equation (2) or equation (9), and equation (10). And N of unknown numbers for determining the variation with time $a_J(\alpha_J, \gamma_J, \gamma_J, - - - , t)$ of the above-described accumulated amount for each radiopharmaceutical $A_J$ is obtained based on the first variation with time measured at a plurality of points, and the above-described equation (2) or equation (9) and equation (10). And thus, the function of the accumulated amount deriving part 14 determines the variation with time $a_J(\alpha_J, \beta_J, \gamma_J, - - - , t)$ of the accumulated amount for the radiopharmaceutical $A_J$ in a certain pixel for each radiopharmaceutical $A_J$ by obtaining the N of unknown numbers $\alpha_J, \beta_J, \gamma_J, - - -$.

In detail, the variation with time of the accumulated amount by the radiopharmaceutical $A_J$ in a certain pixel, that is, the function of the accumulated amount $a_J(\alpha_J, \beta_J, \gamma_J, - - -, t)$ (here, J=1, 2, - - - , M−1, and M, and $\alpha_J, \beta_J, \gamma_J, - - -$ are N of unknown numbers) by the radiopharmaceutical $A_J$ in a certain pixel may be represented with the above-described equation (3) etc. Three unknown numbers $\alpha_J, \beta_J, \gamma_J,$ for determining the function of the accumulated amount $a_J(\alpha_J, \beta_J, \gamma_J, - - - , t)$ are obtained based on the first variation with time obtained by measurement for at least (M×3) of points, and the above-described equation (2) or equation (9), and equation (10), and thus the three unknown numbers $\alpha_J, \beta_J, \gamma_J,$ are obtained. Thereby, the function of the accumulated amount deriving part 14 obtains the function of the accumulated amount $a_J(\alpha_J, \beta_J, \gamma_J, - - - , t)$ for each radiopharmaceutical $A_J$.

A variety of radiopharmaceuticals to be administered may be the same nuclide with each other, and they may also be different nuclides with each other as described above. Accordingly, the data for nuclear medicine obtained by administration of a variety of radiopharmaceuticals may include the data obtained by administration of the radiopharmaceutical of the same nuclide at points of time shifted with each other, and it may also include the data obtained by administration of the radiopharmaceuticals of different nuclides with each other. In the Example 1, the case in the above-described equations (1) to (8) by administration point of time without shifting, and the case of different nuclide with each other at shifted administration points of time as shown in equations (10) and (12) include the data obtained by administration of the radiopharmaceuticals of different nuclide with each other. The cases as shown in the above-described equations (9) and (11) that are cases by the same nuclide and at shifted points of administration time include the data obtained by administration of the radiopharmaceuticals of the same nuclide with each other.

Example 2

Figure 4:
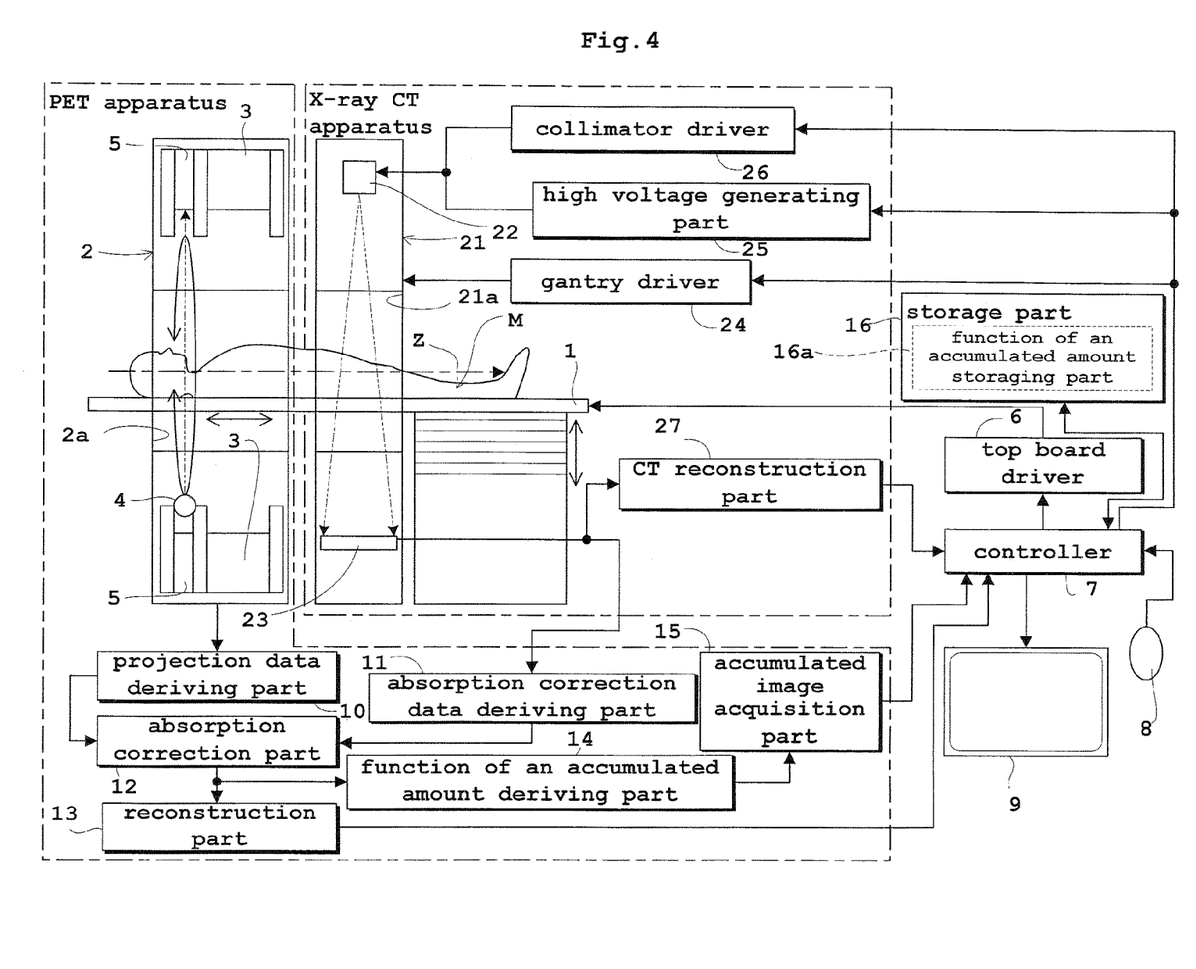
FIG. 4 illustrates a side view and a block diagram of a diagnostic system comprising a PET apparatus, and an X-ray CT apparatus of a PET-CT in Example 2.

Hereinafter, Example 2 of the present invention will be described with reference to drawings. FIG. 4 is a side view and a block diagram of a diagnostic system provided with a PET apparatus and an X-ray CT apparatus of PET-CT according to Example 2.

In the above-described Example 1, the PET apparatus has a point radiation source 4. The point radiation source 4 emits the same γ ray as by a radiopharmaceutical, and the γ ray transmits through the subject M, and thereby the absorption correction data are obtained as a form information based on the radioactive rays. This Example 2 uses a projection data for CT as an absorption correction datum.

The X-ray CT apparatus comprises a gantry 21 having an opening 21a, an X-ray tube 22, and an X-ray detector 23. The X-ray tube 22 and the X-ray detector 23 are disposed mutually facing with each other, sandwiching the subject M, and they are embedded in the gantry 21. Many detecting elements constituting the X-ray detector 3 are disposed around the body axis Z of the subject M in a shape of a fan.

In addition, the X-ray CT apparatus has a gantry driver 24, a high voltage generating part 25, a collimator driver 26, and a CT reconstruction part 27. The CT reconstruction part 27 is configured for the controller 7 to perform, for example, programs stored in a ROM of a storage medium represented by the above-described storing part 16 etc., or commands inputted by the input part 8. Incidentally, the projection data for CT, the tomogram images for CT processed by the CT reconstruction part 27, mentioned later, are written and stored in a RAM of the storing part 16 as in the above-described Example 1 and are read from the RAM if needed. The projection data for CT and the tomogram images for CT are equivalent to the data for X-ray CT in the present invention.

The gantry driver 24 is a mechanism for rotating the X-ray tube 22 and the X-ray tube detector 23 around the body axis Z of the subject M within the gantry 21, while maintaining a mutual facing relationship with each other. The gantry driver 24 comprises a motor etc., not shown.

A high voltage generating part 25 generates a tube voltage and a tube current of the X-ray tube 22. The collimator driver 26 is a mechanism for establishing an X-ray irradiation visual field, and for driving the collimator (not shown) disposed close to the X-ray tube 22 in a horizontal direction. The collimator driver 26 comprises a motor etc., not shown.

In case of an indirect conversion type X-ray detector 23, X-rays emitted from the X-ray tube 22 and transmitted through the subject M are converted into a light by a scintillator (not shown) in the X-ray detector 23, and the converted light is then photo-electric converted by a photosensitive film (not shown) to be outputted as an electric signal. In the case of a direct conversion type X-ray detector 23, the X-rays are directly converted into an electric signal by a radioactive rays sensitive film (not shown) to be outputted. The electric signal is then sent into the CT reconstruction part 27 as an image information (pixel).

The image information sent into the CT reconstruction part 27 is then transmitted as a projection data for CT.

The projection data for CT has a form information as in the absorption correction data in Example 1, and in the Example 2, the projection data for CT is sent into the absorption correction data deriving part 11 so as to be used as an absorption correction data, and simultaneously also into the CT reconstruction part 27.

The image information (projection data for CT) sent into the CT reconstruction part 27 is reconstructed to obtain a tomogram image for CT. This tomogram image for CT is then sent into the output part 9 through the controller 7. Since each function of the processing part in the following step of the PET apparatus containing the absorption correction data deriving part 11 (the absorption correction part 12, the reconstruction part 13, the function of the accumulated amount deriving part 14, and the accumulated image acquisition part 15) are the same as those of Example 1, descriptions thereof will be omitted. The tomogram image for the PET reconstructed by the reconstruction part 13 and the tomogram image for CT reconstructed by the CT reconstruction part 27 may be outputted in a superimposed condition by the output part 9.

In case of the system according to the Example 2, the X-ray CT apparatus obtains the data for X-ray CT based on the X-rays emitted out from the outside of the subject and transmitted through the subject, and the PET apparatus acquires the accumulated images of each radiopharmaceutical, respectively.

Also in the system according to the Example 2, in the same manner as that in the PET apparatus according to Example 1, the input part 8 may have a function for inputting a plurality of information about the data for nuclear medicine.

Also in the system according to the Example 2, in the same manner as that in the PET apparatus according to Example 1, the output part 9 may have a function for output displaying of the accumulated image of each radiopharmaceutical acquired by the accumulated image acquisition part 15 separately, or a function for changing colors for superimposed output.

The present invention is not limited to the above-described embodiments, and operation based on deformation may be carried out as follows.

(1) In each of the above-described Examples, description has been given using a PET apparatus as an example, the present invention is applicable to a SPECT (Single Photon Emission CT) apparatus for reconstructing a tomogram image of a subject according to detection of a single γ ray, etc.

(2) The above-described each Example is an example of a static type apparatus wherein the γ ray detector 3 for projection data including the scintillator block 3a and the photomultiplier 3b detects the γ ray in a static condition. The apparatus may be a rotating type wherein the scintillator block 3a and the photomultiplier 3b detects the γ ray while rotating around the subject M.

(3) In the above-described Example 1, the PET apparatus has the point radiation source 4, the point radiation source 4 emits the same γ ray as the radiopharmaceutical to make the γ ray transmit the subject M, and the absorption correction data are obtained as the form information based on the radioactive rays. In the above-described Example 2, the absorption correction was performed in each Example, respectively, using the projection data for CT as the absorption correction data. However, it is not always necessary to perform the absorption correction. Accordingly, in this case, the data without the absorption correction may be used for the data for nuclear medicine that is the object of the first variation with time.

(4) In the above-described each Example, although the data for nuclear medicine that is the object of the first variation with time is the projection data of the image information (total dose of the γ ray), the first variation with time that is the variation with time of the data for nuclear medicine may be measured using the other data as the data for nuclear medicine.

(5) The above-described each Example has the function of the accumulated amount storing part 16a that stores beforehand the function of the accumulated amount of each radiopharmaceutical, and specified the radiopharmaceutical in the accumulated image, based on the function of the accumulated amount of each radiopharmaceutical beforehand stored by the function of the accumulated amount storing part 16a. However, when the accumulated image is only acquired, without specifying the radiopharmaceutical, it is not always necessary for the apparatus to have the function of the accumulated amount storing part 16a.

(6) As in the above-described each Example, when the number of radiopharmaceutical to be administered is set to M, and the number of unknown number to be obtained for the second variation with time for every radiopharmaceutical is set to N, the number of measurement is not in particular limited in the first measuring device for measuring the first variation with time, in case of measuring the first variation with time at a plurality of points. Incidentally, when taking into consideration of (M×N) of the unknown numbers in total, it is more preferred to measure the first variation with time at points at least (M×N). However, when a predetermined period of time has passed after administration of the radiopharmaceutical and the accumulation function has converged to an unknown number $\alpha_J$, M of unknown numbers smaller than the (M×N) of unknown numbers may just be obtained, and therefore measurement only at M of points should just be performed.

(7) The above-described each Example has a premise of the accumulated amount being saturated, and the function of the accumulated amount $a_J(\alpha_J, \beta_J, \gamma_J, ---, t)$ is an exponential function (exp) like the above-described equations (3), (7) and (8) or the $\alpha_J$ that is a result of convergence. When the radiopharmaceutical is the FDG, the degree of increase of the accumulated amount decrease, and diverges without being saturated. In this case, the function of the accumulated amount $a_J(\alpha_J, \beta_J, \gamma_J, ---, t)$ may just be expressed using a logarithm (log), without using the exponential function. In this way, the shape of the detailed equation of the function of the accumulated amount $a_J(\alpha_J, \beta_J, \gamma_J, ---, t)$ is not in particular limited.

What is claimed is:

1. A nuclear medicine diagnosis apparatus for obtaining data for nuclear medicine of a subject based on radioactive rays generated from the subject having radiopharmaceuticals administered thereto, comprising:
   a first measuring device for measuring a first variation with time that is a variation with time of the data for nuclear medicine obtained by a variety of radiopharmaceuticals having been administered;
   a deriving device for obtaining a second variation with time, for each radiopharmaceutical, that is a variation with time of an accumulated amount by the radiopharmaceuticals in the subject based on the first variation with time; and
   an acquiring device for acquiring an accumulated image of each radiopharmaceutical based on the second variation with time,
   wherein the first measuring device for measuring the first variation with time measures the first variation with time at a plurality of points, when a number of radiopharmaceutical administered is set to M, and a number of unknown number for determining the second variation with time for every radiopharmaceutical is set to N, and
   wherein when the first variation with time is a variation with time of a total dose of the radioactive rays obtained by M of the radiopharmaceuticals being administered;
   a Jth radiopharmaceutical is set to $A_J$ (where, J=1, 2, ---, M−1, M), a variation with time of a dose rate by a radiopharmaceutical $A_J$ is set to $F_J(t)$ (where, J=1, 2, ---, M−1, M), a variation of an accumulated amount in the radiopharmaceutical $A_J$ that exists in a certain pixel for the second variation with time is set to $a_J(\alpha_J, \beta_J, \gamma_J, ---, t)$ (where, J=1, 2, ---, M−1, M and $\alpha_J, \beta_J, \gamma_J, ---$ are N of unknown numbers), and a variation with time of a total dose is set to E(t), then the total dose $\int E(t)dt$ of a certain pixel in a certain period width, is represented with a first equation of $\Sigma_{J=1}^{M}\{\int a_J(\alpha_J,\beta_J,\gamma_J, ---, t)F_J(t)dt\} = \int E(t)dt$, and the deriving device for obtaining the second variation with time determines the variation $a_J(\alpha_J, \beta_J, \gamma_J, ---, t)$ of the accumulated amount in the radiopharmaceutical $A_J$ that exists in a certain pixel for each radiopharmaceutical $A_J$, by determining the N of unknown numbers $\alpha_J$, $\beta_J$, $\gamma_J$, - - - for obtaining the variation with time $a_J(\alpha_J, \beta_J, \gamma_J, ---, t)$ of the accumulated amount for each radiopharmaceutical $A_J$ based on the first variation with time measured at the plurality of points and based on the first equation, and by determining of the unknown numbers $\alpha_J$, $\beta_J$, $\gamma_J$, - - - .

2. The nuclear medicine diagnosis apparatus according to claim 1, further comprising a storing device for the function of the accumulated amount that has stored beforehand the function of the accumulated amount of each radiopharmaceutical, and specifies the radiopharmaceutical in the accumulated image based on the function of the accumulated amount of each radiopharmaceutical that has been stored beforehand by the storing device for the function of the accumulated amount.

3. The nuclear medicine diagnosis apparatus according to claim 1, wherein the variation with time $a_J(\alpha_J, \beta_J, \gamma_J, ---, t)$, that is the second variation, of the accumulated amount based on the radiopharmaceutical $A_J$ that exists in a certain pixel (where, J=1, 2, - - -, M−1, and M, and $\alpha_J$, $\beta_J$, $\gamma_J$, - - - are N unknown numbers) is a function of an accumulated amount that varies with progress of time, the function of the accumulated amount $a_J(\alpha_J, \beta_J, \gamma_J, ---, t)$ is represented with a second equation of $a_J(\alpha_J, \beta_J, \gamma_J, ---, t)=\alpha_J\exp(\beta_J t)+\gamma_J$ represented with the three unknown numbers $\alpha_J$, $\beta_J$, and $\gamma_J$, and the three unknown numbers of $\alpha_J$, $\beta_J$, and $\gamma_J$ for obtaining the function of the accumulated amount $a_J(\alpha_J, \beta_J, \gamma_J, ---, t)$ is obtained based on the first variation with time measured at least (M×3) of points and the first equation to determine the three unknown numbers $\alpha_J$, $\beta_J$, $\gamma_J$, and thereby the deriving device for obtaining the second variation with time obtains the function of the accumulated amount $a_J(\alpha_J, \beta_J, \gamma_J, ---, t)$ for each radiopharmaceutical $A_J$.

4. The nuclear medicine diagnosis apparatus according to claim 3, wherein only unknown number $\alpha_J$ for each radiopharmaceutical $A_J$ is obtained by setting the function of the accumulated amount $a_J(\alpha_J, \beta_J, \gamma_J, ---, t)$ to $\alpha_J$, and thus the deriving device for obtaining the second variation with time obtains the function of the accumulated amount $\alpha_J$ for each radiopharmaceutical $A_J$.

5. The nuclear medicine diagnosis apparatus according to claim 1, wherein in case of use of a radiopharmaceutical $A_I$ (where, I=1, 2, - - -, M−1, M) and $A_J$ (where, J=1, 2, - - -, M−1, and M, and I≠J), when the radiopharmaceuticals $A_I$ and $A_J$ are administered at administration point of times shifted with each other, and the shifted administration time is set to t0 based on a point of time of administration of the radiopharmaceutical $A_J$, a variation with time of a dose rate by the radiopharmaceutical $A_I$ is represented with $F_I(t-t_0)$, and simultaneously a variation with time of a dose rate by the radiopharmaceutical $A_J$ is represented with $F_J(t)$.

6. The nuclear medicine diagnosis apparatus according to claim 5, wherein when two radiopharmaceuticals $A_I$ and $A_J$ are used, and the radiopharmaceuticals $A_I$ and $A_J$ are the same nuclides with each other, a total dose $\int E(t)dt$ of a pixel is represented with the first equation, $\int a_J(\alpha_J, \beta_J, \gamma_J, ---, t)\{k \cdot F_I(t-t_0)+C_1\}dt+\int a_J(\alpha_J, \beta_J, \gamma_J, ---, t)F_J(t)dt=\int E(t)dt$ (where, k and $C_1$ are constants), N of unknown numbers $\alpha_J$, $\beta_J$, $\gamma_J$, - - - for obtaining a variation with time of an accumulated amount for each radiopharmaceutical $A_I$ and $A_J$ of $a_J(\alpha_J, \beta_J, \gamma_J, ---, t)$ is obtained based on the first variation with time measured at a plurality of points, and based on the first equation, and by thus obtaining the N of unknown numbers $\alpha_J$, $\beta_J$, $\gamma_J$, - - -, the deriving device for obtaining the second variation with time can obtain the variation of the accumulated amount $a_J(\alpha_J, \beta_J, \gamma_J, ---, t)$ for each of the radiopharmaceuticals $A_I$ and $A_J$ that exists in a certain pixel for each of the radiopharmaceuticals $A_I$ and $A_J$.

7. The nuclear medicine diagnosis apparatus according to claim 5, wherein when two radiopharmaceuticals $A_I$ and $A_J$ are used, and the radiopharmaceuticals $A_I$ and $A_J$ are different nuclides with each other, the total dose $\int E(t)dt$ of a pixel is represented with the first equation $\int a_J(\alpha_J, \beta_J, \gamma_J, ---, t)\{F_I(t-t_0)+C_2\}dt+\int a_J(\alpha_J, \beta_J, \gamma_J, ---, t)F_J(t)dt=\int E(t)dt$ (where, $C_2$ is a constant), N of unknown numbers $\alpha_J$, $\beta_J$, $\gamma_J$, - - - for obtaining the variation with time of the accumulated amount for each radiopharmaceutical $A_I$ and $A_J$ of $a_J(\alpha_J, \beta_J, \gamma_J, ---, t)$ is obtained based on the first variation with time measured at a plurality of points, and based on the first equation, and by thus obtaining the N of unknown numbers $\alpha_J$, $\beta_J$, $\gamma_J$, - - -, the deriving device for obtaining the second variation can obtain the variation with time of the accumulated amount $a_J(\alpha_J, \beta_J, \gamma_J, ---, t)$ for each of the radiopharmaceuticals $A_I$ and $A_J$ that exists in a certain pixel for each of the radiopharmaceuticals $A_I$ and $A_J$.

8. The nuclear medicine diagnosis apparatus according to claim 1, wherein the data for nuclear medicine obtained by administration of a variety of radiopharmaceuticals include the data obtained by administration of radiopharmaceuticals of a same nuclide at points of time shifted with each other.

9. The nuclear medicine diagnosis apparatus according to claim 1, wherein the data for nuclear medicine obtained by administration of a variety of radiopharmaceuticals include the data obtained by administration of radiopharmaceuticals of different nuclides with each other.

10. The nuclear medicine diagnosis apparatus according to claim 1, wherein the nuclear medicine diagnosis apparatus comprises an input device for inputting a plurality of information about the data for nuclear medicine.

11. The nuclear medicine diagnosis apparatus according to claim 1, wherein the nuclear medicine diagnosis apparatus comprises an output device for separately output-displaying the accumulated image of each radiopharmaceutical acquired by the acquiring device for acquiring the accumulated image, or comprises an output device for changing a color and for superimposed output-displaying.

12. A diagnostic system including a nuclear medicine diagnosis apparatus, the system comprising a nuclear medicine diagnosis apparatus and an X-ray CT apparatus, the nuclear medicine diagnosis apparatus obtaining data for nuclear medicine of a subject based on radioactive rays generated from the subject having a radiopharmaceutical administered thereto, the X-ray CT apparatus obtaining data for the X-ray CT based on X-rays having been emitted from outside of the subject and having transmitted through the subject, the nuclear medicine diagnosis apparatus comprising:

a first measuring device for measuring a first variation with time that is a variation with time of data for nuclear medicine obtained by a variety of radiopharmaceuticals having been administered;

a deriving device for obtaining a second variation with time, for each radiopharmaceutical, that is a variation with time of an accumulated amount by the radiopharmaceuticals in the subject based on the first variation with time; and an acquiring device for acquiring an accumulated image of each radiopharmaceutical based on the second variation with time, wherein the first measuring device for measuring the first variation with time measures the first variation with time at a plurality of points, when a number of radiopharmaceutical administered is set to M, and a number of unknown number for determining the second variation with time for every radiopharmaceutical is set to N, and wherein when the first variation with time is a variation with time of a total dose of the radioactive rays obtained by M of the radiopharmaceuticals being administered;

a Jth radiopharmaceutical is set to $A_J$ (where, J=1, 2, - - -, M−1, M), a variation with time of a dose rate by a radiopharmaceutical $A_J$ is set to $F_J(t)$ (where, J=1, 2, - - -, M−1, M), a variation of an accumulated amount in the radiopharmaceutical $A_J$ that exists in a certain pixel for the second variation with time is set to $a_J(\alpha_J, \beta_J, \gamma_J, $ - - - , t) (where, J=1, 2, - - -, M−1, and M, and $\alpha_J, \beta_J, \gamma_J,$ - - - are N of unknown numbers), and a variation with time of a total dose is set to E(t), then the total dose $\int E(t)dt$ of a certain pixel in a certain period width, is represented with a first equation of $$\Sigma_{J=1}^{M}\{\int a_J(\alpha_J,\beta_J,\gamma_J,\text{- - -},t)F_J(t)dt\}=\int E(t)dt,\text{ and}$$

the deriving device for obtaining the second variation with time determines the variation $a_J(\alpha_J, \beta_J, \gamma_J,$ - - -, t) of the accumulated amount in the radiopharmaceutical $A_J$ that exists in a certain pixel for each radiopharmaceutical $A_J$, by determining the N of unknown numbers $\alpha_J, \beta_J, \gamma_J,$ - - - or obtaining the variation with time $a_J(\alpha_J, \beta_J, \gamma_J,$ - - -, t) of the accumulated amount for each radiopharmaceutical $A_J$ based on the first variation with time measured at the plurality of points and based on the first equation, and by determining the N of the unknown numbers $\alpha_J, \beta_J, \gamma_J,$ - - - .

13. The diagnostic system according to claim 12, wherein the data for nuclear medicine obtained by administration of the plurality of radiopharmaceuticals includes data obtained by administration of radiopharmaceuticals of a same nuclide at points of time shifted with each other.

14. The diagnostic system according to claim 12, wherein the data for nuclear medicine obtained by administration of the plurality of radiopharmaceuticals includes data obtained by administration of radiopharmaceuticals of different nuclides with each other.

15. The diagnostic system according to claim 12, wherein the diagnostic system comprises an input device for inputting a plurality of information about data for nuclear medicine.

16. The diagnostic system according to claim 12, wherein the diagnostic system comprises an output device for separately output-displaying the accumulated image of each radiopharmaceutical acquired by the acquiring device for acquiring the accumulated image, or an output device for changing a color and for superimposed outputting.

17. A nuclear medicine diagnosis apparatus for obtaining data for nuclear medicine of a subject based on radioactive rays generated from the subject having radiopharmaceuticals administered thereto, comprising:

a first measuring device for measuring a first variation with time that is a variation with time of the data for nuclear medicine obtained by a variety of radiopharmaceuticals of mutually different nuclides having been administered at a same administration period of time;

a deriving device for obtaining a second variation with time, for each radiopharmaceutical, that is a variation with time of an accumulated amount by the radiopharmaceuticals in the subject based on the first variation with time; and an acquiring device for acquiring an accumulated image of each radiopharmaceutical based on the second variation with time.

18. The nuclear medicine diagnosis apparatus according to claim 17, wherein the second variation with time is a function of an accumulated amount that varies with progress of time, the apparatus comprises a storing device for the function of the accumulated amount that has stored beforehand the function of the accumulated amount of each radiopharmaceutical, and specifies the radiopharmaceutical in the accumulated image based on the function of the accumulated amount of each radiopharmaceutical that has been stored beforehand by the storing device for the function of the accumulated amount.

19. The nuclear medicine diagnosis apparatus according to claim 17, wherein the first measuring device for measuring the first variation with time measures the first variation with time at a plurality of points, when a number of radiopharmaceutical administered is set to M, and a number of unknown number for determining the second variation with time for every radiopharmaceutical is set to N.

20. The nuclear medicine diagnosis apparatus according to claim 19, wherein when the first variation with time is a variation with time of a total dose of the radioactive rays obtained by M of the radiopharmaceuticals being administered;

a Jth radiopharmaceutical is set to $A_J$ (where, J=1, 2, - - -, M−1, M), a variation with time of a dose rate by a radiopharmaceutical $A_J$ is set to $F_J(t)$ (where, J=1, 2, - - -, M−1, M), a variation of an accumulated amount in the radiopharmaceutical $A_J$ that exists in a certain pixel for the second variation with time is set to $a_J(\alpha_J, \beta_J, \gamma_J,$ - - -, t) (where, J=1, 2, - - -, M−1, and M, and $\alpha_J, \beta_J, \gamma_J,$ - - - are N of unknown numbers), and a variation with time of a total dose is set to E(t), then the total dose $\int E(t)dt$ of a certain pixel in a certain period width, is represented with a first equation of $$\Sigma_{J=1}^{M}\{\int a_J(\alpha_J,\beta_J,\gamma_J,\text{- - -},t)F_J(t)dt\}=\int E(t)dt,\text{ and}$$

the deriving device for obtaining the second variation with time determines the variation with time $a_J(\alpha_J, \beta_J, \gamma_J,$ - - -, t) of the accumulated amount in the radiopharmaceutical $A_J$ that exists in a certain pixel for each radiopharmaceutical $A_J$, by determining the N of unknown numbers $\alpha_J, \beta_J, \gamma_J,$ - - - for obtaining the variation with time $a_J(\alpha_J, \beta_J, \gamma_J,$ - - -, t) of the accumulated amount for each radiopharmaceutical $A_J$ based on the first variation with time measured at the plurality of points and based on the first equation, and by determining the N of the unknown numbers $\alpha_J, \beta_J, \gamma_J,$ - - - .

21. The nuclear medicine diagnosis apparatus according to claim 20, wherein the variation with time $a_J(\alpha_J, \beta_J, \gamma_J,$ - - -, t), that is the second variation, of the accumulated amount based on the radiopharmaceutical $A_J$ that exists in a certain pixel (where, J=1, 2, - - - ; M−1, and M, and $\alpha_J, \beta_J, \gamma_J,$ - - - are N unknown numbers) is a function of an accumulated amount that varies with progress of time, the function of the accumulated amount $a_J(\alpha_J, \beta_J, \gamma_J,$ - - -, t) is represented with a second equation of $a_J(\alpha_J, \beta_J, \gamma_J,$ - - -, t)=$\alpha_J \cdot \exp(\beta_J \cdot t) + \gamma_J$ represented with the three unknown numbers $\alpha_J, \beta_J,$ and $\gamma_J$, and the three unknown numbers of $\alpha_J, \beta_J,$ and $\gamma_J$ for obtaining the function of the accumulated amount $a_J(\alpha_J, \beta_J, \gamma_J,$ - - -, t) is obtained based on the first variation with time measured at least (M×3) of points and the first equation to determine the three unknown numbers $\alpha_J, \beta_J, \gamma_J,$ and thereby the deriving device for obtaining the second variation with time obtains the function of the accumulated amount $a_J(\alpha_J, \beta_J, \gamma_J,$ - - -, t) for each radiopharmaceutical $A_J$.

22. The nuclear medicine diagnosis apparatus according to claim 21, wherein only unknown number $\alpha_J$ for each radiopharmaceutical $A_J$ is obtained by setting the function of the accumulated amount $a_J(\alpha_J, \beta_J, \gamma_J, ---, t)$ to $\alpha_J$, and thus the deriving device for obtaining the second variation with time obtains the function of the accumulated amount $\alpha_J$ for each radiopharmaceutical $A_J$.

23. The nuclear medicine diagnosis apparatus according to claim 17, wherein the nuclear medicine diagnosis apparatus comprises an input device for inputting a plurality of information about the data for nuclear medicine.

24. The nuclear medicine diagnosis apparatus according to claim 17, wherein the nuclear medicine diagnosis apparatus comprises an output device for separately output-displaying the accumulated image of each radiopharmaceutical acquired by the acquiring device for acquiring the accumulated image, or comprises an output device for changing a color and for superimposed output-displaying.

25. A diagnostic system including a nuclear medicine diagnosis apparatus, the system comprising a nuclear medicine diagnosis apparatus and an X-ray CT apparatus, the nuclear medicine diagnosis apparatus obtaining data for nuclear medicine of a subject based on radioactive rays generated from the subject having a radiopharmaceutical administered thereto, the X-ray CT apparatus obtaining data for the X-ray CT based on X-rays having been emitted from outside of the subject and having transmitted through the subject, the nuclear medicine diagnosis apparatus comprising:

a first measuring device for measuring a first variation with time that is a variation with time of data for nuclear medicine obtained by a variety of radiopharmaceuticals of mutually different nuclides having been administered at a same administration period of time;

a deriving device for obtaining a second variation with time, for each radiopharmaceutical, that is a variation with time of an accumulated amount by the radiopharmaceuticals in the subject based on the first variation with time; and an acquiring device for acquiring an accumulated image of each radiopharmaceutical based on the second variation with time.

26. The diagnostic system according to claim 25, wherein the diagnostic system comprises an input device for inputting a plurality of information about data for nuclear medicine.

27. The diagnostic system according to claim 25, wherein the diagnostic system comprises an output device for separately output-displaying the accumulated image of each radiopharmaceutical acquired by the acquiring device for acquiring the accumulated image, or an output device for changing a color and for superimposed outputting.

* * * * *